United States Patent

Matte et al.

[11] Patent Number: 5,558,839
[45] Date of Patent: Sep. 24, 1996

[54] MAGNETIC DEVICE FOR IMMUNOLOGICAL ANALYSIS OF A SOLID PHASE

[75] Inventors: Claude Matte, Paris; Anne Muller, Gif/Yvette, both of France

[73] Assignee: Pasteur Sanofi Diagnostic, Marnes La Coquette, France

[21] Appl. No.: 209,274

[22] Filed: Mar. 14, 1994

Related U.S. Application Data

[62] Division of Ser. No. 916,494, Jul. 21, 1992, Pat. No. 5,318,914.

[30] Foreign Application Priority Data

Jul. 22, 1991 [FR] France .................. 91 09242

[51] Int. Cl.⁶ .................................................. B01L 11/00
[52] U.S. Cl. ...................... 422/101; 209/217; 210/222; 366/274; 422/99; 436/529; 436/806
[58] Field of Search ....................... 436/518, 526, 436/806, 824, 531; 209/214, 217, 226; 210/222, 695; 422/99, 101, 68.1; 366/273, 274

[56] References Cited

U.S. PATENT DOCUMENTS

| 3,693,941 | 9/1972 | Suchy | 366/274 |
|---|---|---|---|
| 4,080,663 | 3/1978 | Wik | 366/274 |
| 4,085,037 | 4/1978 | Quets et al. | 210/695 |
| 4,272,510 | 6/1981 | Smith et al. | 427/47 |
| 4,568,195 | 2/1986 | Herz et al. | 366/274 |
| 4,911,555 | 3/1990 | Saffer et al. | 366/274 |
| 4,916,081 | 4/1990 | Kamada et al. | 436/526 |
| 4,988,618 | 1/1991 | Li et al. | 210/695 |

FOREIGN PATENT DOCUMENTS

| 0262760 | 4/1988 | European Pat. Off. . |
| 0351857 | 1/1990 | European Pat. Off. . |
| 0417301 | 3/1991 | European Pat. Off. . |
| 8705536 | 9/1987 | WIPO . |

Primary Examiner—Robert J. Warden
Assistant Examiner—Jan M. Ludlow
Attorney, Agent, or Firm—Jacobson, Price, Holman & Stern, PLLC

[57] ABSTRACT

An apparatus for performing immunoassays employs a microtiter tray having wells coated with a specific binding partner in conjunction with an array of magnets disposed below the tray. A device for providing relative circular motion of the tray and magnetic array so as to provide a magnet field to the well walls for attracting magnetic particles and subsequent movement of the magnetic field.

4 Claims, 1 Drawing Sheet

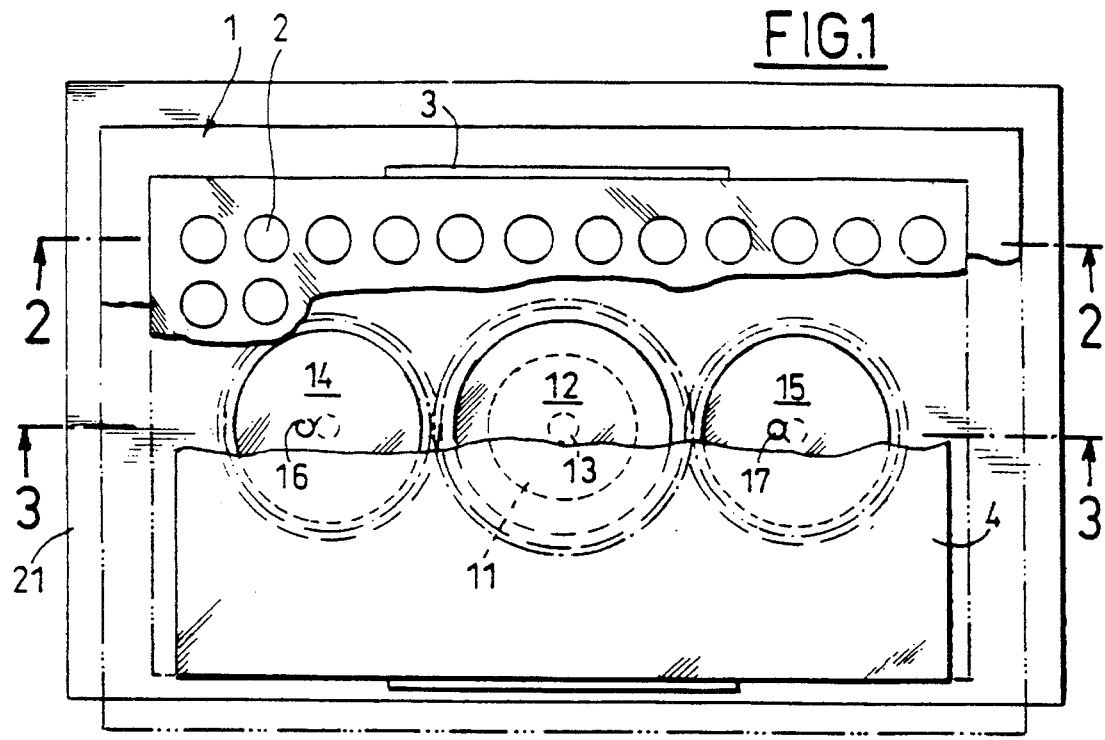
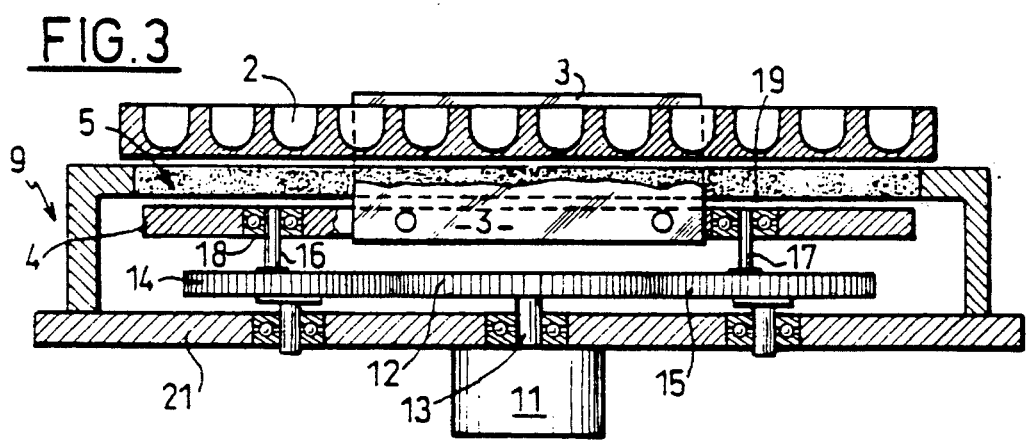
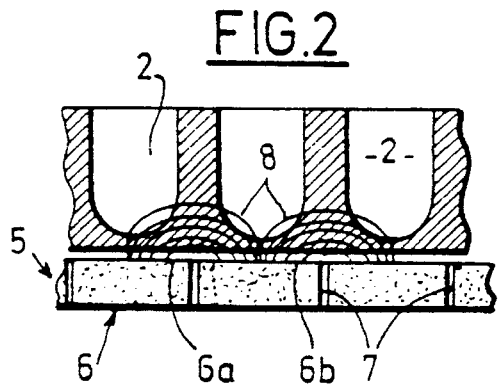
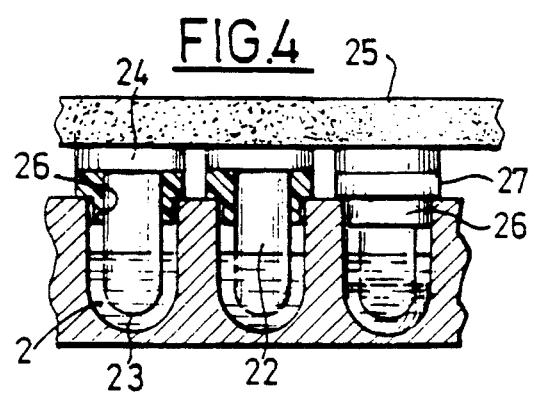

MAGNETIC DEVICE FOR IMMUNOLOGICAL ANALYSIS OF A SOLID PHASE

This application is a divisional of Ser. No. 07/916,494, filed Jul. 21, 1992 now U.S. Pat. No. 5,318,914.

The present invention relates to a process for immunological determination or detection of biological substances, in particular antigens or antibodies, and devices for implementing this process.

Numerous techniques, of varying degrees of sensitivity and specificity, make it possible to detect the presence of antigens or the presence of antibodies in biological media by formation of immunological type bonds between the substance to be determined and one or more known substances.

Some employ an immune adherence phenomenon, described in particular an Amer. J. of Clinical Pathology 82 (6)—719–721 (1984). In this method, the sample to be studied is introduced into a receptacle, generally the cup of a microtitration plate, on whose walls there are molecules or cells which have a specific affinity for the substance to be determined; a suspension of sensitized particles, that is to say on which there is a substance capable of bonding by affinity with the substance to be determined, is also introduced and the distribution of these particles after a dynamic sedimentation phase is studied; in the presence of the substance being tested for, the particles evenly line the walls to which they are bonded via immunological type bonds occurring between the substance fixed onto the wall, that to be determined and the substance present on the particle; an even film is observable on the bottom of the cup; in the absence of the substance being tested for the particles collect at the bottom, around the point of convergence of the walls, by forming a more opaque central spot. It is obvious that in the absence of an external force applied to the particles, their sedimentation would be too slow for the process to find application in routine fast biological analysis and it is known that a suitable centrifugation makes it possible to accelerate this type of sedimentation, but it requires the use of bulky specific precision equipement which requires fine adjustment; as a matter of fact, on the one hand, the centrifugal force applied must be exactly parallel to the axis of symmetry of the receptacles, to avoid having different distribution profiles according to the position of the receptacle relatively to the axis of rotation and, on the other hand, the centrifugation conditions must, in order to obtain good sensitivity and to avoid false results, be fixed for each type of substance to be determined and reactant since the duration and the centrifugal force depend on them; furthermore, these techniques employing centrifugation, even if they are used for routine analyses, do not lead themselves to a compact, simple and cheap automation.

It has recently been proposed, in Patent Application WO 90/09590, to accelerate sedimentation of the sensitized particles by the action of a magnetic force instead of a centrifugal force, by using sensitized particles containing a magnetic core—a process which overcomes the drawbacks due to the use of a centrifuge.

Nevertheless, the Applicant has noticed, as will be seen further on, that this technique, in particular described in WO 90/09590, does not make it possible to distinguish clearly reactions which are weakly positive from reactions which are negative, so that it is not sensitive enough for testing for irregular red blood cell antibodies and for antigens during pre-transfusion testing, or for lymphocytic antigens before tissue grafting.

The present invention provides a process which is distinctly more sensitive, specific and fast and can be partially or completely automated since the observation of the particles at the bottom of the receptacles, whether they are transparent or opaque, can be carried out using a photometer while the operations of filling the reaction receptacles, incubating and washing can be carried out with conventional devices, which are known to the skilled man.

The subject matter of the present invention is a process for determining or detecting by immuno adherence a biological substance present in a sample, which consists in introducing the sample into a receptacle on whose walls there is a component which has a specific immunological affinity for the substance to be tested for, in adding magnetic particles on which there is a substance which has a specific immunological affinity for the substance to be tested for, in subjecting them to several successive magnetic actions in order to accelerate the deposition of the said particles onto the walls and to displace those which have not formed specific bonds with the substance to be tested for which has adhered to the walls via the component with affinity which is fixed thereto, and in observing the particles deposited.

In a first embodiment, the process according to the invention consists:

a) in introducing the said sample into a receptacle on whose walls there is a component which has a specific immunological affinity for the substance to be tested for, b) in adding magnetic particles on which there is a substance which has a specific immunological affinity for the substance to be tested for, c) in subjecting the particles to the action of a static magnetic fiels in order to coat the particles onto the walls, and thus to make possible the immunological reaction, d) then in subjecting the receptacle to the action of a magnetic field of variable direction in order to displace and collect at the bottom the particles which are not fixed by specific bonding to the walls via the substance to be tested for and the component with affinity which is firmly fixed to the wall, and finally, e) in observing the particles deposited.

According to another aspect of this first embodiment, the particles are furthermore subjected, before final observation, to a static magnetic field in order to remove from the receptacle the particles which do not adhere thereto via immunological bonds. For instance, it is possible to introduce into the receptacle a suitably magnetized rod onto which only the particles which do not specifically adhere to the walls on the receptacle will form a coat.

In a second embodiment, the process according to the invention consists:

a) in introducing the said sample into a recipient on whose walls there is a component which has a specific immunological affinity for the substance to be tested for, b) in adding magnetic particles on which there is a substance which has an immunological affinity for the said substance to be tested for, c) in subjecting the particles to the action of a static magnetic field in order to bring the particles onto the walls, and thus to make possible the characteristic immunological reaction, d) then in subjecting the receptacle to the action of a static magnetic field, for instance using a suitably magnetized rod, in order to remove from the receptacle the particles which do not adhere to its walls by an immunological type bonding, e) and finally in observing the particles deposited.

In a known manner, the said sample to be studied is in general left to incubate in the sensitized receptacle for a certain time, for example up to 30 minutes, at a temperature between approximately 20° C. and 45° C. before adding the magnetic particles.

A stage of washing between these first two stages of the process of the invention is furthermore in general carried out, in particular when the magnetic particles are sensitized with a substance which would not have an affinity only for the substance to be tested for.

In general, routine immunological determinations are carried out simultaneously in microtitration plates which comprise series of cavities also called cups or wells, sometimes up to about a hundred, with a capacity of approximately 350 µl, arranged in parallel rows, or in cavities aligned on support bars, but any other receptacle of suitable dimensions could be used.

Another subject matter of the present invention is devices for implementing the process according to the invention.

In what follows, the devices according to the invention are described while referring to microtitration plates, but it is understood that the invention is not limited to this type of receptacle, neither to an apparatus comprising a single plate. In these plates, the cups can be flat-bottomed, conical, frustoconical or hemispherical.

A device according the the invention, which is appropriate for implementing the first embodiment of the process, comprises:

a support for keeping a microtitration plate horizontal, and capable of giving the whole of the plate horizontal circular translation movement whose amplitude is between 1 mm and 15 mm in radius, as a function of the dimensions of the cups;

underneath, a set of magnets whose upper poles are parallel to the plate and are either arranged under each cup in a chequered pattern, possibly alternately North and South, the space between them being of the order of at least 2 mm, or advantageously arranged in a strip under each row of cups, the poles of two neighbouring strips being alternately North and South, and the space between two strips being very small, of the order of 1/10 mm or less, it even being possible for the strips to be contiguous.

By circular translation, a movement is understood during which the centre of the receptacle describes a circular path but carries out no rotation around its axis.

According to an alternative embodiment, the device can comprise a stationary plate support, and a set of magnets capable of carrying out a horizontal circular translation movement.

Another device according to the invention, which is appropriate for implementing the variant of the first embodiment or for implementing the second embodiment comprises further a series of magnetized cylindrical rods, of diameter less than that of the cups, and means for introducing them simultaneously into all the cups, along their axis, as far as a small distance from the bottom, for example between 0.1 and 1.5 mm, and removing them therefrom.

These rods can be made of soft iron or steel, treated in order to make them resistant to attack by the reaction medium; they are then during their use in magnetic contact with a permanent magnet, which magnetizes them. It is possible to have a single magnet for all the rods, or a small magnet for each one. Furthermore, each rod can itself be a permanent magnet. The shape of the lower end of the rods is, preferably, adapted to that of the receptacle into which they are introduced—hemispherical, conical or flat, accordingly—but it is also possible, in particular, to use a conical end in a hemispherical cup.

The rods, whose length can be greater than the depth of the cups and which can be wider at the top, are supported by a grating or a plate, as is optionally the case for the permanent magnets.

For implementing the second embodiment of the process, the set of alternate magnets of the first device can be replaced by any means which makes it possible to create, in the zone where the receptacles are, a magnetic field, which will attract the particles towards the walls, such as a uniformly magnetized plate; furthermore, in this case, the microtitration plate support and the magnets are fixed with respect to each other.

The receptacles will be able to be filled and washed manually or using known mechanical means in appropriate work-stations and it will be possible to combine, with the magnetic treatment means according to the invention, conventional means for filling and washing the microtitration plates.

Furthermore, it will be possible to carry out observation of the distribution profiles of the particles with the naked eye, preferably using a magnifying device, such as a binocular magnifying glass, and for very high sensitivities with a suitable photometer coupled to a recording system; in the latter case, as is known, a transparent microtitration plate is used.

In the process according to the invention, the substance to be tested for can be an antigen which is free or bound to the surface of a cell such as a virus, a lymphocyte, a platelet, an erythrocyte or an antibody, directed against a cellular or tissue antigen or against an allergen, presend in serum or in another biological medium.

The substances which have an affinity for the substance to be tested for, that is to say which are capable of forming immunological type bonds with it, are then respectively antibodies or antigens. The capture component, which is immobilised on the walls of the titration receptacle, will have to bind specifically the substance to be determined, whereas the revealing substance, which is on the magnetic particles, could be non specific. Numerous substances with suitable affinity, currently used in immunological analysis, are known, such as polyclonal or monoclonal antibodies, antiglobulins, lectins, red blood cells and vital proteins, and the skilled mand will choose the one which is suitable to the desired determination, without difficulty.

The component fixed on the walls can be an antibody or an antigen, which are free or contained in the membrane of an intact cell or of a stroma or which come from a cell lysate.

The capture component is fixed onto the walls of the cups by techniques which are well known to the specialists, either by absorption, when the cups are made of polystyrene, polyvinyl chloride or polymethacrylate, by covalent chemical bonding with a compound contained in the material of the plate or deposited on the walls of the cups in an adherent film or by any other means known to the specialist, such as the one mentioned in EP-A-0350233 according to which red blood cells are bound via ionic dyes.

On the market there are a number of microtitration plates, said to be sensitized, on whose cups there is the capture component or which are ready to be sensitized by known techniques. The specialist knows that not all plates are suitable for determinations of the type of those of the invention, by immuno adherence; it is obviously desirable, in order that there should not be false positive results or negative results, that the density of the nodding sites is even and such that, the revealing particles are arranged on the walls in a single layer, preferably essentially continuous.

The magnetic particles will be of small size, of the order of 0.5 µm to 5 µm and preferably between 0.8 µm and 1.7 µm and of a fairly homogenous particle size, in general, consisting of a natural or synthetic polymer, which does not spontaneously adhere strongly to the material of the cavities; the polymer can coat a magnetic core or magnetic components such as iron, ferrites and alloys which are dispersed in the polymer bulk. Suitable particles are commercially available, and those of the trade mark Dynabeads® of the company Dynal or those of the trade mark Estapor® of the company Rhone-Poulenc, which are composed of a polystyrene latex, containing up to 40% by weight of ferrite, may be cited. Coloured particles can also be used.

The substance which is on the magnetic particles must have an affinity for the substance to be determined; thus a species-specific anti-immunoglobulin for determining an antibody, or a polyclonal or a monoclonal antibody for determining an antigen, are suitable. They will be fixed on the particle by one of the techniques known to the man skilled in the art, which are similar to those used for fixing on the cup wall; several molecules are in general fixed simultaneously on the same particle, which makes it possible, if the local density of the substances to be determined which are immobilized on the walls is suitable, to obtain excellent adhesion of the particle.

In the first magnetic treatment phase, the titration cups are places in static magnetic fields, whose distribution and intensity are identical for all the cups, and which are directed so that the particles are bring downwards so that they deposit onto the surface of the walls. The magnetic force must be sufficiently intense for the sedimentation to be fast without being excessive, in order to avoid a collection of all the particles at the lowest point, due to their pulling from the walls where they had previously been deposited.

In this phase, when the particles arrive near the sensitized walls, affinity bonds can be created between the revealing substance which is on the particle and the substance to be determined, which is immobilized on the wall via the specific capture component.

In embodiments of the process in which the particles are subjected to the action of a magnetic field of variable direction, during this phase the particles which are weakly, or not, bonded ace pulled out and slide along the walls so that they collect in the lowest zone of the cups.

A preferred means, according to the invention, for varying this direction consists, as previously mentioned, in subjecting the microtitration plate to circular translation movements of small diameter above the set of magnets so that the axis of a cup describes a circle whose centre is located at the intersection of the line joining its axis to the one of a contiguous cup, which is located above a magnet of the opposite polarisation to the one underneath which the cup is placed, with the line of the air-gap between these two magnets; the radius of the said circle is less than half the width of a magnet, preferably between 10 and 40% of this width.

Under these conditions, all the points at the bottom of each receptacle are at one moment above the line of the air-gap, where the magnetic field is at a maximum, or in its vicinity, so that all the particles which are weakly bound are pulled off the walls in a very short time, in less than 5 minutes and even better, in most cases in approximately 2 minutes.

The intensity of the magnetic fields to be applied depends in particular on the size and the density of the particles and on their concentration, on the viscosity of the reaction media, on the intensity of the forces of affinity bonding and on the geometry of the cups, and the skilled man will determine, by prior testing, their value and the suitable durations of the various magnetic treatment phases which depend on them, in order to obtain optimum sensitivity and the absence of false positive and negative results for a reasonable treatment time.

Preferably, the bottom of the cups will be placed at a small distance above the set of magnets, which will make possible the use of magnets of low power, in particular consisting of polymer strips containing magnetized particles, which are found in the trade; this distance will be, in general, of the order of 1 mm, from 0.1 to 5 mm, for magnetic inductions less than 0.5 tesla.

For assays of antigens or antibodies in currently used microtitration plates, of 12.8 cm×8.6 cm comprising 96 cups arranged in 12×8 parallel rows, with magnetic particles of diameter between 0.5 µm and 5 µm and a density less than or equal to approximately 2, the average intensities of magnetic induction under the bottom of the cups are 0.2 to 0.4 tesla, whereas the dipping rods have a diameter of 3 mm, a length of at least 10 mm and they create in the vicinity of their pole piece a magnetic induction of 0.10 to 0.20 tesla. The duration of the first phase of deposition of the particles in the stationary fields is from a few seconds to 5 minutes, whereas the one of displacement in the magnetic fields is less than 5 minutes, about 2 minutes in general, for a rotation speed between 0.5 and 4 revolutions per second; finally, the duration of action of the magnetized rods will be in general from 5 seconds so several minutes, possibly in several successive dips.

The process of the invention, in its various aspects, can be carried our manually, with simplified magnetic treatment equipment, but it can also be carried out in an automatic biological analysis apparatus which comprises, further to the components conventionally present in this type of immuno assay automatic apparatus, at least one magnetic treatment device according to the present invention.

Thus, an automated unit for testing antigens or antibodies by the immuno adherence process of the invention comprises a sample loader, a work-station for filling the microtitration plate cups with the samples and the reactants, comprising the magnetic particles in suspension, am incubating-station, a washing-station, as well as a work-station for performing the magnetic treatments according to the invention and a work-station for photometric reading wherein the observation, whether quantitative or not, of the particles deposited in the cups, is done, the various work-stations being under the control of a microcomputer in charge of the various stages of the assay and its interpretation.

In order to make the invention better understood, particular embodiments will be described with reference to the attached figures in which:

FIG. 1 represents a devide according to the invention in a plan view, with partial cutaway, FIG. 2 represents, in a section along 2—2 and in a blown-up view, a part of the device showing the microtitration plate and the magnets, during the initial static magnetic treatment, FIG. 3 represents, in a section along 3—3, the device according to FIG. 1, FIG. 4 represents, in section and in a blown up view, a part of a device used for implementing one variant.

FIGS. 1 to 3 represent a device for implementing the process according to the invention according to its first embodiment, comprising magnetic treatment means for carrying out determinations by immune adherence using microtitration plates.

The device represented in FIGS. 1 to 3 comprises a microtitration plate 1 comprising a set of cups 2. This plate is fixed horizontally on the two parts of a support 3, which is itself fixed onto a plate 4 arranged horizontally which will be described in more detail further on with reference to FIG. 3.

As represented in FIG. 2, beneath the microtitration plate 1, at a small distance from and parallel to this plate, is a set 5 of magnets 6 in the shape of strips arranged under each row of cups 2 and whose upper poles are alternatively North 6a and South 6b, a very small space 7 (air-gap) being left between two strips.

The static magnetic field prevailing above the magnets 6 is represented symbolically at 8.

The set 5 of magnets 6 is fixed to a parallelepipedal frame 9 under which a motor 11 is fixed.

The motor 11 drives a central cog wheel 12 via an axle 13. The motor cog wheel engages the lateral cog wheels 14, 15, on each of which there is a small eccentric axle 16, 17 serving as a hub for the ballbearings 18, 19.

These bearings are set in the plate 4 which will therefore be driven in a circular translation movement when the cog wheels carrying the small eccentric axles 16, 17 rotate.

The cog wheels 12, 14, 15 are mounted on the lower plate 21 of the frame 9.

In order to apply the static magnetic field the arrangement of the magnets as represented in FIG. 1 is used. The static magnetic field makes it possible to bring the particles which are introduced into the cups 2 upon the walls.

In order to apply the magnetic field of variable direction, the motor 11 is started rotating and the titration plate 1 which is fixed to the plate 4 is subjected to circular translation movements.

These circular translation movements of the cups 2 above the magnetic fields make it possible to obtain within the cups 2, not only a magnetic field of variable direction, but also a slight agitation of the contents of the cups 2, which contributes to the separation of the particles which are not bound or are weakly bound.

Preferably, before carrying out the circular translation movement, the microtitration plate 1 is displaced with respect to the system of magnets, parallel to a row of cups, in the direction of alternation of the poles of magnets 6a and 6b, over a length approximately equal to half the distance between the axis of the cups; by this means, the axis of each receptacle is, during the rotations, nearer the zone of the air-gaps 7, where the magnetic field is at a maximum. The support is obviously provided with a means which makes this short translation possible.

In a particularly preferred embodiment, the axis of each receptacle is positioned at the beginning above the air-gap 7.

In FIG. 4, a device is represented which is appropriate for implementing the variant of the first embodiment of the process or for implementing the second embodiment of the process.

The device represented in FIG. 4 comprises a set of magnetized cods 22 arranged in the same arrangement as the cups 2. Each rod 22 is made of soft iron or steel; it is of cylindrical shape; it has a hemispherical lower end 23 and an upper end 24 in contact with a permanent magnet 25.

This device is intended to be introduced into the cups 2 of the microtitration plate after this plate has been subjected to a static and/or rotating magnetic field and when each cup is still filled with the reaction medium. The magnetized rods 22 are lowered using means which are not shown and introduced into the cups 2 until the lower ends 23 of the rods are a short distance from the bottom of the cups. The adjustment of the distance and the centring of the rods 22 are ensured by conventional means which are not shown.

The magnetized rods exert an attractive force in a direction which is substantially opposite to the one of the first (static) magnetic field on the deposited particles, but only those which are not fixed or are weakly fixed by immunological bonds onto the walls of the cups 2 will be removed.

In what follows, a description is given of examples of implementing the process according to the invention, using the devices for magnetic treatment of a microtitration plate which were described previously, for detection of red blood cell irregular antibodies in serum, as well as, for comparison, the results obtained during a magnetic sedimentation under the action of a constant field, as described in Patent Application WO 90/09590, previously cited, or with the test marketed by the company Immucor Inc.—Norcross—U.S.A. under the trade mark Capture R® which involves a centrifugation.

This latter test for detection of irregular antibodies is carried out by an immuno adherence technique, in plates to which there have been fixed "test" (reference) red cells which are known to bear the antigens corresponding to the antibodies to be detected. This process involves:

distributing the samples to be tested and the controls in the sensitized cavities, a fairly long incubation of approximately 20 minutes, 6 successive washings with an isotonic solution in order to eliminate all undesirable substances, addition of revealing red blood cells, that is to say onto which anti-human immunoglobulin antibodies have been fixed, a centrifugation, in a centrifuge for a microtitration plate with cavities, lasting one minute at 1000 g, then observing the distribution profiles of the red blood cells at the bottom of the cups; all the operations carried out manually for a complete plate require approximately 1 hour.

The process according to the invention is distinctly more sensitive than these two known techniques.

EXAMPLE 1

Determination of an Irregular Red Blood Cells Antibody a) Preparation of the magnetic particles coated with anti-human globulin.

Brown, latex magnetic particles of the trade mark Estapor® marketed by Rhone-Poulenc (particle size 0.8 um) are washed with an aqueous solution of KOH (pH 9–10) then suspended at a concentration of 1.2% (w/V) in a GBS buffer, composed of 0.1M glycine and 0.14M NaCl and adjusted to pH 8.2 by adding NaOH.

A solution of an anti-human IgG antibody of concentration 0.2 mg/ml, is furthermore prepared, in the same buffer.

The solution and the suspension are mixed in equal volumes and kept for 45 minutes, under agitation at 37° C.

The sensitized particles are then separated and washed copiously with the GBS buffer containing 0.1% of bovine serum albumin.

b) Preparation of the antibody solutions to be studied.

Dilutions are prepared, in a geometric progression of common ratio 2, of a stock solution containing 1% (w/V) of an anti-D antibody, in an aqueous solution of NaCl (0.9%-w/V) containing bovine serum albumin (6%-w/V).

c) Determination of the antibodies.

In the assays which follow, a polystyrene microtitration plate 12.8 cm×8.6 cm, whose 96 cups are U-shaped and are pretreated in order to fix red blood cells, is used; this plate is marketed by Immucor Inc. under the trade mark Capture R®.

A suspension of washed reagent blood cells of concentration 0.5% (w/V) bearing the antigen corresponding to the antibody to be determined, is distributed in the cups; the plate is centrifuged and the cups washed with saline solution, then 50 ul of each dilution of the antibody solution with 100 ul of the appropriate aqueous low ionic strength solution are introduced therein. In some of the cups, a negative control is introduced which is constituted of inert human serum of group AB.

The plate is incubated for 20 minutes at 37° C. and then the cups are repeatedly washed with an aqueous solution of NaCl (0.9%-w/V). Then 50 µl of the previously prepared suspension of magnetic particles, brought to a concentration of 0.02% in a GBS pH 8.2 buffer to which is added 0.1% of bovine serum albumin, are introduced therein.

The plate is then put down onto the magnetic treatment device represented in FIGS. 1 to 3, whose characteristics are the following: set of magnets formed of strips of Ferriflex® (rubber filled with magnetic particles) marketed by the company DIC (France), of thickness 5 mm, width 9 mm and length 70 mm, located less than 0.8 mm under the bottom of the cups, arranged in parallel rows and so that the axes of the cups are aligned on the middles of the strips or even better on the air-gaps.

The plate is left for 2 seconds on its support, then the support of the plate is driven for 2 minutes in a rotational movement whose radius is 3 mm at a speed of approximately 50 revolutions per minute.

The distribution of the particles on the bottom of the cups is then observed with the naked eye: in the case of a negative reaction a large brown pellet is observed in the middle of the bottom of the cup, whereas in the case of a positive reaction a brown film is observed over the entire bottom.

The negative control is further clearly distinguished from the cups containing anti-D at a dilution of 1/128 which was previously prepared from the 1% stock solution.

By way of comparison, an assay was carried out with a sensitized microplate in the same way and with the same dilutions but using, instead of the sensitized magnetic particles, sensitized red blood cells marketed by the company Immucor for its Capture-R® test: the magnetic treatment phase was replaced by a centrifugation of the plate for 1 min at 1000 g, as recommended by this company; it was then possible to distinguish with the eye positive-result and negative result cups only up to a dilution of $1/32$nd of the stock solution.

Sensitized plates were also prepared as previously, as well as 4.5 um Dynabeads® magnetic particles marketed by Dynal under the reference M 450, coated with anti-human immunoglobulin, applying the method described in Example 1 of Patent Application WO 90/09590 and 25 µl of these particles were introduced into the cups containing the anti-D dilutions. The plate was then treated as described in Example 1 of the said application (homogenisation on a micro-agitator then action of a static magnetic field). The last dilution giving a positive-result distribution which was barely observable with the naked eye is the one of $1/16$, whereas with the same particles subjected to the magnetic treatment described in the present example, a distinct distribution is observable up to $1/32$ with difference making interpretation very easy.

Finally sensitized Estapor® magnetic particles of 0.8 µum were used, and they were subjected to the magnetic treatment described in WO 90/09590; the figures obtained were uninterpretable since the negative control itself does not give the expected pellet at the bottom of the cup, even if the duration of action of the magnetic field is extended up to 30 minutes, whereas the same particles, subjected to the magnetic treatment of the invention, give difference up to $1/128$.

EXAMPLE 2

The microplates are prepared as in Example 1 but the magnetic treatment is carried out in three steps, the first two steps being identical to those of the preceding example; during the third, for two minutes, magnetized rods are previously described, of diameter 3 mm, are introduced into each cup. After withdrawal of the rods, a positive-result distribution is then distinguished with a binocular magnifying glass up to a dilution of $1/1024$th of the 1% stock solution.

EXAMPLE 3

The magnetic treatment of the prepared plates as in Example 1 is such as to perform only the first and the third steps of the treatment described in Example 2.

Observation with a suitable photometer allows the presence of a positive-result distribution to be noticed up to a dilution of $1/256$th of the 1% stock dilution.

EXAMPLE 4

Reverse ANO Grouping, So-Called Simonin Test

A suspension of 0.02% (w/V) of Estapor® 0.8 µm magnetic particles coated with anti-human globulins is prepared, as well as microtitration plates coated with capture red blood cells as in Example 1 but of groups A1, A2 and B. 50 µl of plasma to be studied and 10 µl of low ionic strength solution are introduced into each cup and incubation is carried out for 20 minutes at 37° C. The cups are then washed and 50 µl of suspension of magnetic particles are introduced therein, before subjecting the plate to a magnetic treatment in two steps as in Example 2. Observation of the distributions obtained allowed determination, without error, of the group A, B, AB or O of the plasma studied.

EXAMPLE 5

Forward ABO Grouping, So-Called Beth Vincent Test

In this assay, a polystyrene microtitration plate is used whose U-shaped cups are pretreated in order for them to be able to fix red blood cells, by the method described in Methods of Enzymology. vol 73, CH Heusser, JW Stocke, RH Gisler, Academic Press Inc. (1981)

A suspension is prepared, as in Example 1, or 0.02% (w/v) of Estapor® magnetic particles, of 0.8% um diameter, but coated with anti-murine globulins.

50 µl of a 1% (w/v) suspension of the red blood cells to be studied, which have been previously washed, are distributed in 3 cups per sample and the plate is left for 5 minutes at room temperature before washing the cups with saline solution. Into one of the three cups of each sample, 50 µl of murine anti-A est serum and 100 µl of low ionic strength solution are introduced; into another, 50 µl of murine anti-B test serum and the same quantity of low ionic strength solution are introduced, and into the third cup, anti-A+B test serum as well as a low ionic strength solution are introduced. After 20 minutes of incubation at 37° C., the cups are washed and 50 µl suspension of magnetic particles is introduced into each one, before subjecting the plate to a magnetic treatment in three steps as in Example 2.

Observation of the distribution of the magnetic particles made it possible to determine without error the group A, B, AB or O of each of the 70 samples, of which some had a weak antigenicity, being groups $A_3$, $A_3B$, Ax, $B_3$ or Bh.

EXAMPLE 6

Determination of IgG-Type Immuno-Globulins

A suspension of magnetic particles sensitized with an anti-human IgG antibody is prepared as in Example 1.

Moreover, the 96 cups of a rigid polystyrene microtitration plate, marketed by the company Polylabo (France) under the reference M 24 A, are coated with a goat anti-human IgG antibody as follows: 100 µl of an aqueous solution with 2.2 mg/ml of anti-IgG are introduced and left to incubate for 1 hour at 37° C. and one night at 4° C. After elimination of the liquid, the cavities are filled with GBS buffer containing 0.1% of bovine serum albumin, and it is left in contact for one night at 4° C., then it is washed copiously with an aqueous solution of NaCl at 0.9% (w/V). The samples to be studied, of concentration 1 µg/ml, are prepared by dissolving immunoglobulin IgG marketed by Sigma under the reference I 4506 in an aqueous solution of NaCl (0.9%) containing 2% of serum albumin; the negative control samples only contain the diluent. Into each cup of the plate, 100 µl of sample are introduced and left to incubate for 45 minutes at 37° C. before washing with a saline solution.

50 µl of the suspension of magnetic particles brought to a concentration of 0.02% in a GBS buffer—pH 8.2, to which is added 0.1% of bovine serum albumin, are introduced into each cup, and the plate is subjected to the magnetic treatment described in Example 2. Positive-result cups are distinguished perfectly from negative-result cups with the naked eye.

EXAMPLE 7

Detection of Irregular Red Blood Cell Antibodies

The solutions of magnetic particles and the solutions of the serums or plasmas to be studied which contain irregular antibodies dilutions up to 1/2048th) are prepared as in Example 1.

On the one hand 26 sera or plasmas containing irregular alloantibodies of C, c, E, D, K, Kpb, Fya, Fyb, Jka, Jkb, S or Lub specificity and, on the other hand, 170 so-called negative plasmas which are known to contain no irregular antibody are studied.

The cups are pretreated as in Example 5, then 50 µl of a 1% (w/v) suspension of the reagent red blood cells, whose specificity with respect to the antibody to be tested for is known, is introduced into the cups, which are washed after standing 5 minutes at room temperature.

For the study of plasmas containing the irregular antibodies, a cup with reagent red blood cells on which there is the antigen corresponding to the antibody being tested for, and a cup with reagent red blood cells which do not contain this antigen, are prepared for each example.

For the study of undiluted negative plasmas, one cup contains reagent red blood cells on which there is the whole range or blood-group antigens.

Into the washed cups, 50 µl of the solution to be studied and 100 µl of low ionic strength solution are introduced, and they are left to incubate for 20 minutes at 37° C. The cups are then washed before 50 µl of the suspension of magnetic particles is introduced therein and the plate is subjected to the treatment in three steps described in Example 2, before observing the distribution of the particles either with the eye or with a photometer.

No false positive reaction was detected on the negative plasmas, which shows the good specificity of the process.

The titers, that is to say the last dilution for which a positive reaction was observed, for the antibody samples studied, are given in Table I.

The determination of the titer on a serum containing anti-D antibody was repeated 10 times on several occasions; no significant difference for the 1/128 titer was observed.

By way of comparison, a determination of the 26 irregular antibody samples was carried out with the kit marketed under the Immucor trade mark Capture R. It was noticed that the process according to the invention gave, for 56% of the samples, a net increase in sensitivity corresponding to a titer difference of 1 to 3.

TABLE 1

| SAMPLE No. | SPECIFICITY | TITER | |
|---|---|---|---|
| 1 | anti-c | | 4 |
| 2 | anti-c + E | | 2048 |
| 3 | anti-D + C | (for D | 128 |
|   |            | (for E | 32 |
| 4 | anti-E | | 128 |
| 5 | anti-Fya | | 64 |
| 6 | anti-JKb | | 256 |
| 7 | anti-Kell | | 64 |
| 8 | anti-D | | >2048 |
| 9 | anti-Kpb | | 128 |
| 10 | anti-Lub | | 32 |
| 11 | anti-D | | 128 |
| 12 | anti-S | | 16 |
| 13 | anti-c + E | | 512 |
| 14 | anti-E | | 256 |
| 15 | anti-E | | 64 |
| 16 | anti-c + Kell | (for K | 64 |
|    |              | (for c | 64 |
| 17 | anti-Fya | | 4 |
| 18 | anti-E + $C^w$ | (for E | 32 |
| 19 | anti-Fyb | | 16 |
| 20 | anti-JKa | | 32 |
| 21 | anti-E | | 8 |
| 22 | anti-Kell | | 256 |
| 23 | anti-Fya | | 256 |
| 24 | anti-c | | 128 |
| 25 | anti-D + Fya | (for D | 64 |
| 26 | anti-E + Kell | (for K | 64 |
|    |              | (for E | 1024 |

We claim:

1. A device for use in an immunoassay, wherein a substance which specifically binds a biological substance to be assayed in a sample, immobilized on magnetic particles, is reacted with the sample in wells of a microtitration plate coated with a component which specifically binds the biological substance, and the distribution of the particles as an indication of the presence or absence of the biological substance is observed, said device comprising:

a horizontal microtitration plate having wells arranged in a zone, each well having a coating that can specifically bind the biological substance, and having supporting means comprising means for causing the plate to execute horizontally a circular translation movement, a set of magnets positioned under the well zone, each magnet having upper and lower vertically aligned poles, with the upper poles disposed in a plane parallel to the plate and arranged in a checkered pattern of alternating poles or lines of alternating poles, said magnets arrayed so as to provide at least one magnetic field for attracting magnetic particles to at least a portion of a wall of each said well, when the supporting means is in a first position.

2. The device according to claim 1 wherein said magnets comprise magnetized polymer.

3. A device for use in an immunoassay, wherein a substance which specifically binds the biological substance to be assayed in a sample, immobilized on magnetic particles, is reacted with the sample in wells of a microtitration plate coated with a component which specifically binds the biological substance, and the distribution of the particles as an indication of the presence or absence of the biological substance is observed, said device comprising:

a horizontal microtitration plate having wells arranged in a zone, each well having a coating that can specifically bind the biological substance, and having motionless supporting means, a set of magnets positioned under the well zone, each magnet having upper and lower vertically aligned poles, with the upper poles disposed in a plane parallel to the plate and arranged in a checkered pattern of alternating poles or lines of alternating poles, said magnets arrayed so as to provide at least one magnetic field for attracting magnetic particles to at least a portion of a wall of each said well when the set of magnets is in a first position, means for causing the set of magnets to execute a horizontally relative circular translation movement with respect to the supporting means.

4. The device according to claim 3 wherein said magnets comprise magnetized polymer.

* * * * *